(12) United States Patent
Ginter et al.

(10) Patent No.: US 7,645,235 B2
(45) Date of Patent: Jan. 12, 2010

(54) METHOD FOR EFFECTING LOCAL INCREASES IN TEMPERATURE INSIDE MATERIALS, PARTICULARLY BODY TISSUE

(75) Inventors: Siegfried Ginter, Stutensee (DE); Marko Liebler, Bretten (DE); Thomas Dreyer, Karlsruhe (DE); Rainer Riedlinger, Karlsruhe (DE)

(73) Assignee: Richard Wolf GmbH, Knittlingen (DE)

( * ) Notice: Subject to any disclaimer, the term of this patent is extended or adjusted under 35 U.S.C. 154(b) by 322 days.

(21) Appl. No.: 10/523,334

(22) PCT Filed: Jul. 29, 2003

(86) PCT No.: PCT/DE03/02537

§ 371 (c)(1),
(2), (4) Date: Jan. 28, 2005

(87) PCT Pub. No.: WO2004/014488

PCT Pub. Date: Feb. 19, 2004

(65) Prior Publication Data

US 2006/0173388 A1    Aug. 3, 2006

(30) Foreign Application Priority Data

Jul. 30, 2002    (DE) ................................ 102 34 533

(51) Int. Cl.
*A61B 10/00* (2006.01)
(52) U.S. Cl. ........................ 600/437; 600/438; 600/439; 600/443; 600/447; 600/449
(58) Field of Classification Search ............... 601/2–4; 600/443, 447, 437, 438, 439
See application file for complete search history.

(56) References Cited

U.S. PATENT DOCUMENTS

| | | | |
|---|---|---|---|
| 4,807,633 A * | 2/1989 | Fry | ............................. 600/438 |
| 4,905,671 A | 3/1990 | Senge et al. | |
| 6,962,587 B2 * | 11/2005 | Johnson et al. | ............... 606/41 |
| 2002/0077627 A1 * | 6/2002 | Johnson et al. | ............... 606/41 |

FOREIGN PATENT DOCUMENTS

| | | |
|---|---|---|
| EP | 0 619 104 B1 | 10/1994 |
| WO | WO 93/19705 A1 | 10/1993 |
| WO | WO 02/32506 A1 | 4/2002 |

OTHER PUBLICATIONS

G. Wojcik, et al., Nonlinear Modeling of Therapeutic Ultrasound, IEEE Ultrasonics Symposium, 1995, p. 1617-1622.

(Continued)

*Primary Examiner*—Brian Casler
*Assistant Examiner*—Baisakhi Roy
(74) *Attorney, Agent, or Firm*—Cohen Pontani Lieberman & Pavane LLP (57) ABSTRACT

Local tissue areas should be thermally destroyed when using ultrasound thermotherapy. Traditionally, mono-frequency continuous wave ultrasound signals are used to this end. These lead to a non-optimal distribution of heat or to a non-optimal localization of the heating inside the tissue. In practice, the following dosage problem arises: the prevention of unwanted tissue damage in the tissue located in front of the target area while simultaneously having a sufficiently high damaging effect in the target area. The aim of the invention is to optimize the distribution of heat or to increase the localization of the heating. To these ends, modified transmitted signals (e.g. multi-frequency signals) are used that are adapted to a specific utilization of the non-linear ultrasound propagation and attenuation properties inside the tissue. This enables, while limited to the target area, a non-linear heating yield caused by non-linear ultrasound effects to be achieved that drastically improves the localization of the heating. Due to this optimization, the problem of dosage is substantially eased, and it is possible to thermally destroy even deep-lying tumors without unwanted burning of the tissue located in front of the tumors. This results in both improving the practical usability of ultrasound thermotherapy and in further reducing the side effects thereof.

17 Claims, 4 Drawing Sheets

Non-linear steepening of a CW-sine signal

OTHER PUBLICATIONS

D. R. Daun and K. Hynynen, A 256-Element Ultrasonic Phased Array System For The Treatment Of Large Volumes Of Deep Seated Tissue. *IEEE Trans. Ultras. Ferro. Freq. Control*, 46(5):1254-1268, 1999.

F. A. Duck, Physical Properties of Tissue, Academic Press, London 1990, pp. 98-101, Tables 4.13, 4.14, 4.15, and 4.16.

F. Feng, C. Zhu, J. Xu, Z. Chen, and H. Li. Enhancement of ultrasonic cavitation yield by a bifrequency irradiation and its frequency effect. *Proceedings of the 135th Meeting of the ASA*, Seattle, USA, vol. III, pp. 1715-1716. Acoustical Society of America, Jun. 1998.

E.A. Filonenko, Effect Of Acoustic Nonlinearity On Heating Of Biological Tissue By High-Intensity Focused Ultrasound. *Acoustical Physics*, 47(4):468-475, 2001.

K. Fujimoto, Y. Ishibashi, M. Shibata, T. Suzuki, S. Aida, N. Ioritani, S. Shirai, and S. Orikasa. A new cavitation suppression technique for local ablation using high-intensity focused ultrasound. In *IEEE Ultrasonic Symposium—1995*, pp. 1629-1632, 1995.

S. Ginter, Numerical Simulation Of Ultrasound-Thermotherapy Combining Nonlinear Wave Propagation With Broadband Soft-Tissue Absorption. *Ultrasonics*, 37:693-696, 2000.

C. R. Hill, Optimum Acoustic Frequency For Focused Ultrasound Surgery. *Ultrasound Med. And Biol*, 20(3):271-277, 1994.

C. R. Hill and G. R. ter Haar. Review Article: High Intensity Focused Ultrasound—Potential For Cancer Treatment. *Brit. J. Radiol.*, 68(816):1296-1303, 1995.

V. Khokklova, O. Sapozhnikov, Yu. Pishchalnikov, T. Sinilo, E. Filonenko, M. Bailey, and L. Crum, Enhancement Of Ultrasound-Induced Heating In Tissue Phantoms Due To Formation Of Shocks: Experimental Measurements And Numerical Simulation. Handout: WFUMB 2000, Florence, 2000.

B.-Y. Lu, W.-L. Lin, Y.-Y. Chen, R.-S. Yang, T.-S. Kou, and C.-Y. Wang, A Multifrequency Driving System For Ultrasound Hyperthermia, *IEEE Engineering in Medicine and Biology*, 18(5):106-111, 1999.

G. O. N. Oosterhof, E. B. Cornel, G. A. H. J. Smits, F. M. J. Debruyne, and J. A. Schalken, Influence Of High-Intensity Focused Ultrasound On The Development Of Metastases, *European Urology*, 32(1):91-95, 1997.

R. Rastert, I. Simiantonakis, M. Moosmann, P. Huber, J. Debus, and J. Jenne, Treatment Acceleration By Modification Of Sound Fields And Sonication Modalities. *IEEE Ultrasonics Symposium*, San Juan Puerto Rico, vol. 2 pp. 1441-1444. IEEE Ultrasonics, Ferroelectrics and Frequency Control Society, Oct. 2000.

I. H. Rivens, R. L. Clarke, and G. R. ter Haar, Design of focused ultrasound surgery transducers, *IEEE Trans. Ultras. Ferro. Freq. Control*, 43(6):1023-1031, 1996.

G. Vallancien, E. Chartier-Kastler, N. Bataille, D. Chopin, M. Hargouni, and J. Bougaran, Focused Extracorporeal Pyrotherapy, *European Urology*, 23 (suppl. 1), 1993.

F. Wu, W.-Z. Chen, J. Bai, J.-Z. Zou, Z.-L. Wang, H. Zhu, and Z.-B. Wang, Pathological Changes In Human Malignant Carcinoma Treated With High-Intensity Focused Ultrasound, *Ultrasound Med. And Biol.*, 27(8):1099-1106, 2001.

* cited by examiner

Figure 1:
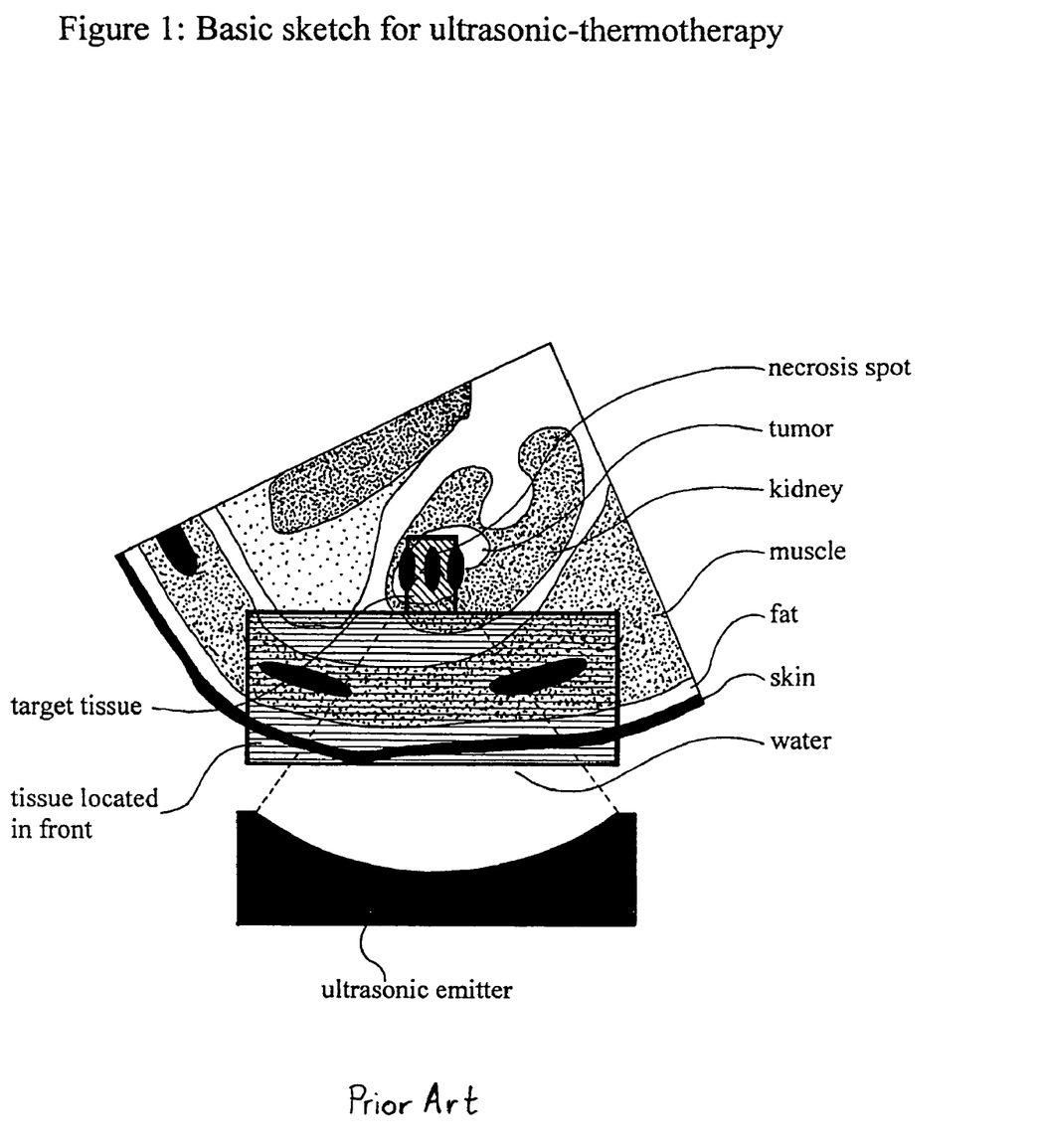

Figure 1: Basic sketch for ultrasonic-thermotherapy

Prior Art

Figure 2:
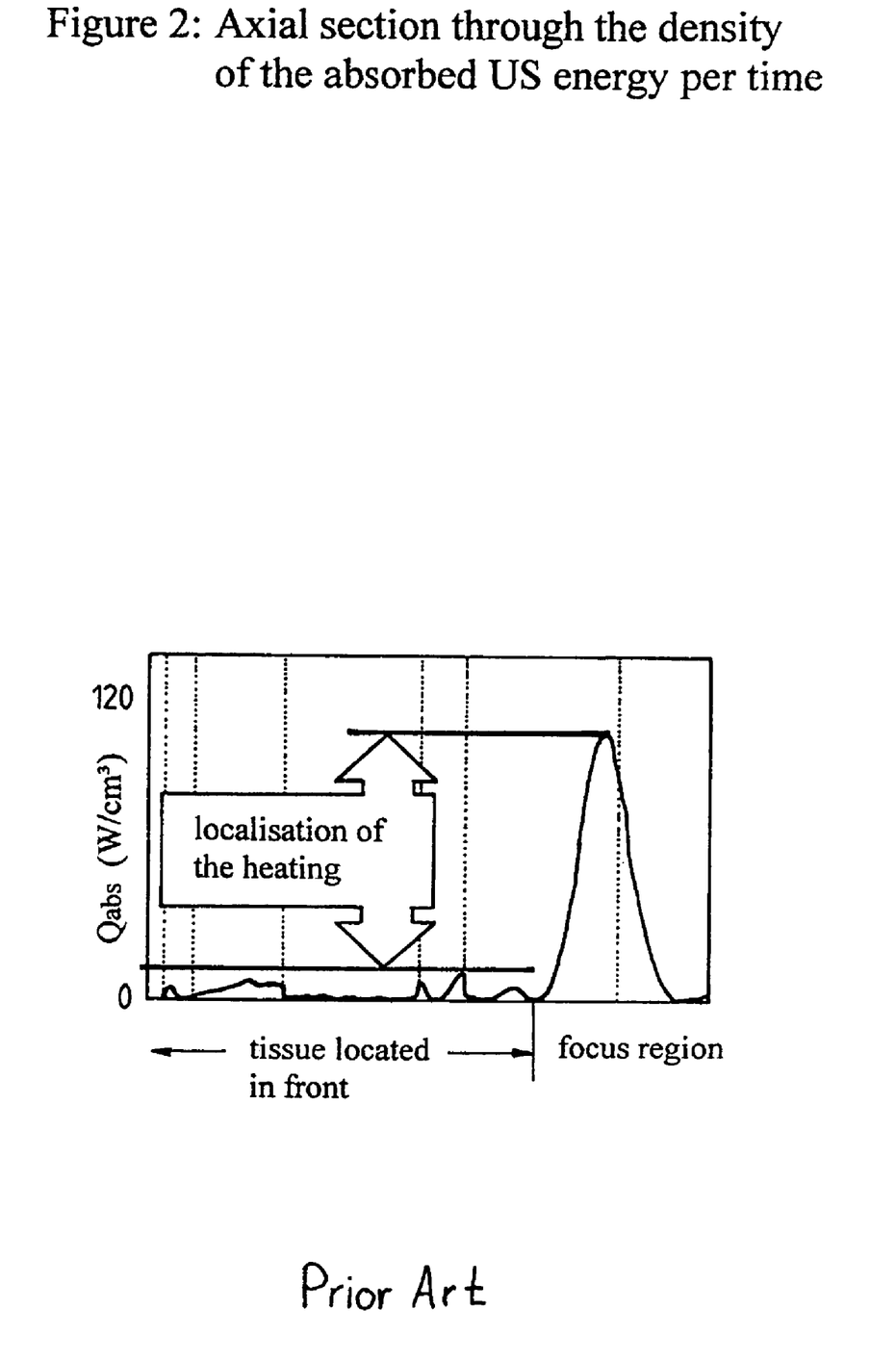

Figure 2: Axial section through the density of the absorbed US energy per time

Prior Art

Figure 3:
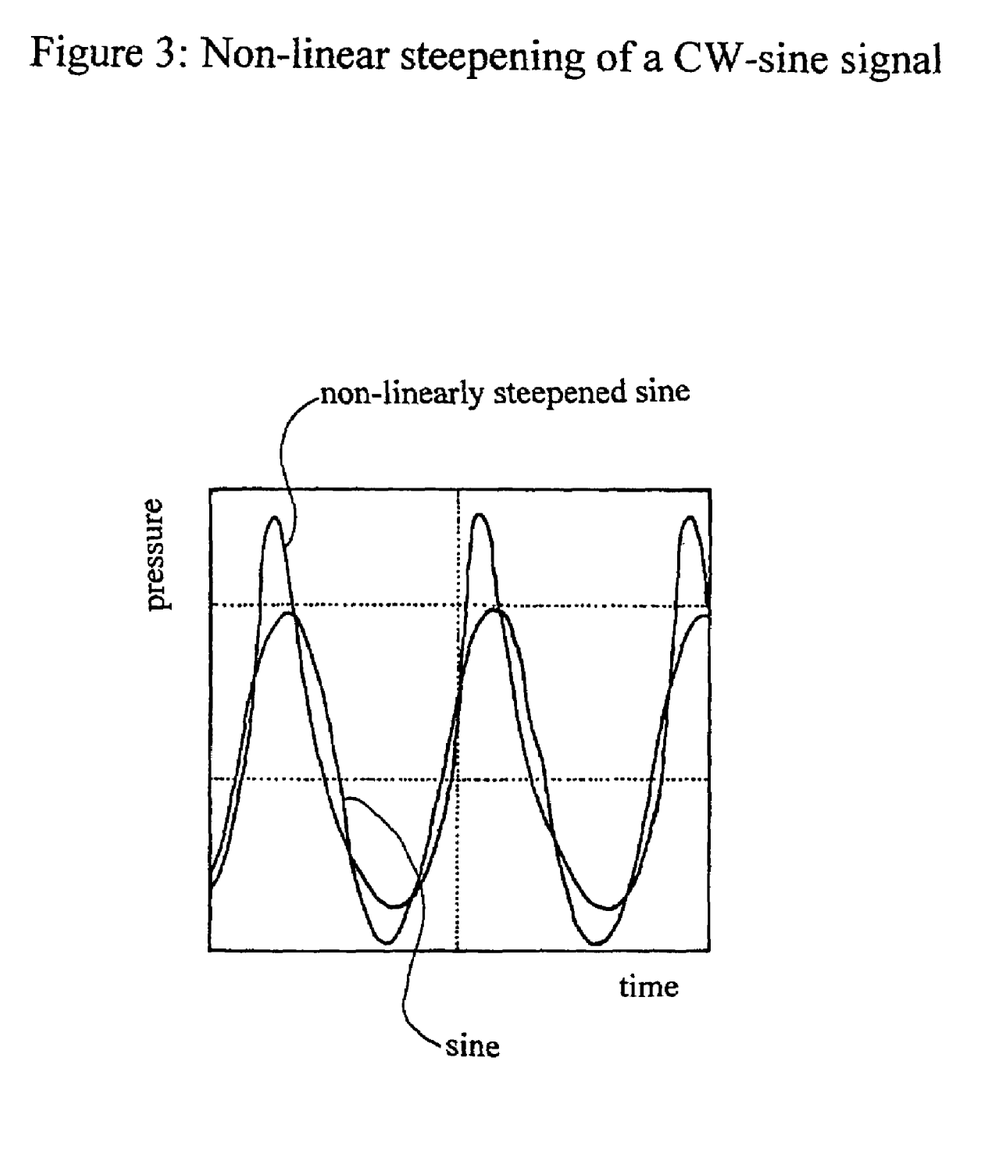

Figure 3: Non-linear steepening of a CW-sine signal

Figure 4:
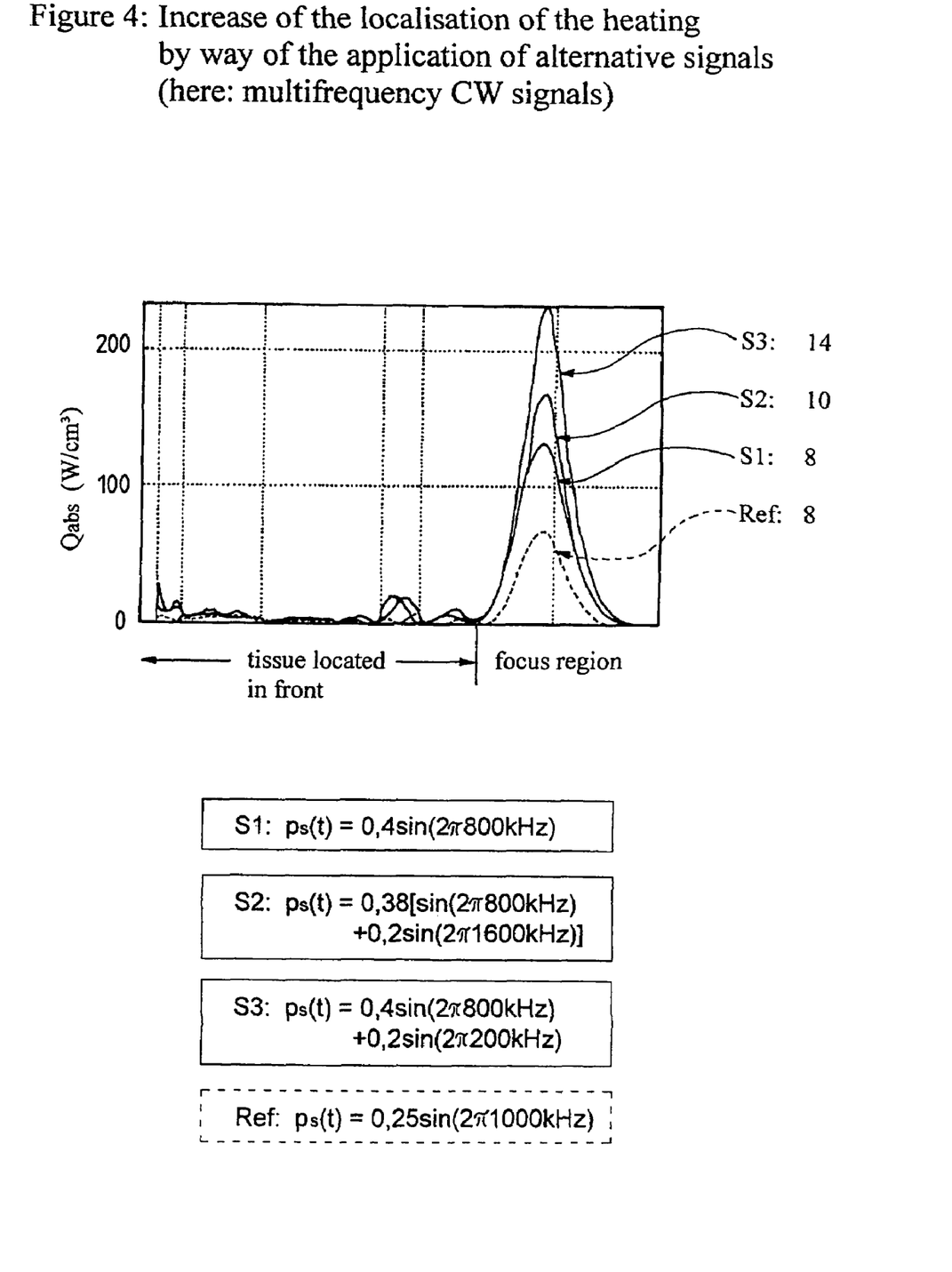

Figure 4: Increase of the localisation of the heating by way of the application of alternative signals (here: multifrequency CW signals)

S1: $ps(t) = 0{,}4\sin(2\pi 800\text{kHz})$

S2: $ps(t) = 0{,}38[\sin(2\pi 800\text{kHz}) + 0{,}2\sin(2\pi 1600\text{kHz})]$

S3: $ps(t) = 0{,}4\sin(2\pi 800\text{kHz}) + 0{,}2\sin(2\pi 200\text{kHz})$

Ref: $ps(t) = 0{,}25\sin(2\pi 1000\text{kHz})$

METHOD FOR EFFECTING LOCAL INCREASES IN TEMPERATURE INSIDE MATERIALS, PARTICULARLY BODY TISSUE

PRIORITY CLAIM

This is a U.S. national stage of application No. PCT/DE2003/002537, filed on 29 Jul. 2003. Priority is claimed on the following application: Country: Germany, Application No.: 102 34 533.3, Filed: 30 Jul. 2002.

BACKGROUND OF THE INVENTION

For the therapy of solid tumors, those treatments which preserve the organ are being used during surgery. In these cases, the therapeutic application of highly intensive ultrasound (US) represents a very promising alternative form of therapy [15, S.1104]. By way of the extracorporal application of highly intensive, focused US (HIFU=High Intensive Focused Ultrasound), one may also thermally destroy tumors situated deep in the body, in a non-invasive manner. Thus the application of HIFU is suitable for a multitude of possible tumor diseases, such as for the treatment of tumors of the breast, the prostate, the kidney, the bladder and the liver [8]. The advantage of therapy with ultrasound in comparison to convention tumor treatment above all lies in the manner of acting which is gentle to the patient and the high acceptance by the patients as a result of this.

The basic manner of acting is shown in FIG. 1. A focusing US-emitter radiates highly intensive ultrasound. The ultrasound is coupled into the body via a prior stretch of water and is concentrated into the focus region. The tumor to be treated is located here. The absorption of the ultrasound in the tissue leads to a heating. The therapeutic effect of the ultrasound field is at its maximum in the focus region. With ultrasonic thermo-therapy (USTT), local temperatures in the tumor of approx. 70-90° C. are desired, which within seconds induce a thermo-necrosis in the focus region (necrosis spot), whilst simultaneously avoiding an overheating of the tissue surrounding the tumor. A complete treatment of the tumor is effected by way of the pointwise joining of individual necrosis spots. The probability of the thermally caused cell death depends on the achieved temperature and its effective duration. Apart from this thermal effect, other mechanical effects e.g. due to cavitation (formation of cavities filled with gas and vapor) are also present.

The application of ultrasound thermo-therapy nowadays entails the following problems:

A targeted local necrosis production demands an exact metering of the therapy in order not to produce any undesired burns, so-called "hot spots" in the tissue located in front or the tissue surrounding the tumor, but despite this needs to achieve an adequate heat in the focus region for the thermo-therapy. This problem with regard to the metering (dosage) is the limiting factor in many fields of application and prevents this therapy from being established quickly. Indeed with the treatment of deeply lying tumors, due to the handling ability of the apparatus or the limitation of the US-window into the human body, as a rule weakly focusing US emitters are applied. These with respect to greatly focusing systems display a significantly worse localization of the heating (FIG. 2). Thus for the application in practice there results only a very limited region for the correct choice e.g. the heating time for the production of a necrosis spot, without leaving behind undesired "hot spots" in the tissue located in front and undesired "cold spots" in the region to be treated. FIG. 2 emphasizes the term of the localization of heating. The localization results as a quotient of the maximum of the heat source in the focus region and the maximum of the heat source in the tissue located in front.

The treatment of a complete tumor is effected by a pointwise joining of individual thermo-necroses (scanning). One problem of ultrasonic thermo-therapy which has not been solved until now is the long therapy duration which has been necessary for the treatment of a large volume of tumor. In order to prevent thermal accumulation effects and thus overheating in the "tissue located in front", a pause duration must be momentarily maintained between the individual ultrasound applications, which drastically increases the actual desired application duration of the therapy.

The question as to whether thermo-ablation by way of focused US leads to an increased metastasization has not been conclusively answered. Up to now however, one may assume that no increased metastasization rate occurs if only thermal energy and no mechanical cavitations occurs in the tumor [11, 14]. For this reason, the mechanical loading of the tissue on account of cavitation must be kept as low as possible.

At present, for heating or for overheating the tissue in USTT, exclusively mono-frequency CW (continuous wave) pressure signals are radiated from the US-emitter. The selection of the amplitude and the frequency of the US-signal is effected in dependency on the position of the tumor on the basis of simple, linear considerations as well as the evaluation of extensive in vitro and in vivo experiments [13, 7]. Since the US-damping typical for soft tissue increases exponentially with the frequency, as a rule for the USTT of tumors close to the surface one selects CW sine signals with higher frequencies and lower amplitudes. If the tumors lie deeper in the tissue, the frequency is usually slightly reduced in order to increase the penetration depth of the US. By way of the reduction of the frequency with a constant aperture of the emitter, the focusing effect for the treatment of deeply lying tissue is weakened further and thus the localization of the heating is worsened even more. The "optimal" amplitudes and frequencies until now have been selected exclusively on account of linear considerations such that the attained heating is only achieved on account of the damping of the base frequency of the signal [13, 7]. In order to avoid undesired cavitation effects, sine signals with low amplitudes are applied. With CW sinusoidal signals the cavitation probability increases with a reducing frequency of the signal and with an increasing pressure amplitude (i.e. also increasing expansion component of the pressure wave). High-pressure amplitudes, which lead to non-liner steepening effects of the US-waves are therefore generally avoided. Thus as a rule only linear effects play a part with regard to heating. This means that on heating deeply lying tissue, as is desired in USTT, and undesirable high thermal loading in the tissue located in front is difficult to avoid.

In order to be able to carry out a change in the emitting frequency depending on the treatment depth without a mechanical exchange of the therapy head, a multi-frequency therapy apparatus has been put forward in the U.S. Pat. No. 5,460,595.

By way of this however, the general metering (dosage) problems with the treatment of deeply lying tumors, such as the undesirable heat accumulation effect in the tissue located in front or the poor localization of the heating are not alleviated.

In [1] a phased array US emitter is suggested with which simultaneously one is able to set several temperature foci in the tissue. It is shown that by way of this the achieved necrosis spot of a scan point is significantly increased and thus the therapy time may be reduced. By way of the targeted broadening of the focal area onto several adjacent foci however, simultaneously the localization of the heating is reduced which further intensifies the problem of metering (dosage). In order to solve this problem in practice, accompanying the therapy, here one must apply a non-invasive monitoring of the temperature, which at the same time is supposed to help in mastering the balancing act with regard to the metering (dosage). For this, apart from picture-providing US one mostly applies MR tomography. This renders the originally inexpensive US therapy method very expensive.

One idea which reduces the heat accumulation in the tissue located in front is based on a special application of the temporally subsequent necrospots on scanning the tumor volume [12]. The choice is selected such that an as large as possible time duration lies between the production of adjacent necrosis spots in which an attenuation of the temperature may be effected. Thus the pause time between the application of the individual necroses may be further reduced.

The ideas based on linear considerations are rigidly coupled to the use of CW sine signals, and on account of the selection of the suitable frequency, permit the attainment of an optimum of the penetration depth and heating on account of linear estimations. This, for the localization of the heating, leads to sub-optimal results. For the practical application of the therapy it means that on the one hand the USTT of deeply lying tumors without expensive monitoring is not possible without "hot spots" or "cold spots". Furthermore, due to the poor localization of the heating one must provide adequate pause time between the individual thermo-necroses for cooling, which for its part unacceptably increases the duration of the therapy. The idea [12] only attempts to alleviate the negative effects of this sub-optimal result on production of a necrosis spot, specifically the undesired increased thermal loading of the tissue located in front, by way of skilful scanning algorithms on treatment of the complete tumor.

None of the above suggestions leads to an improvement of the localization of the heating, i.e. for an increase of the ratio of the maximum of the heat source in the focus region to the maximum of the heat source in the forward situated tissue on production of a necrosis spot.

SUMMARY OF THE INVENTION

An object of the present invention lies in a direct improvement of the localization of the heating with the targeted use of non-linear US propagation effects. By way of this, on the one hand the balancing act on metering (dosing) is drastically alleviated even with deeply lying tumors so that a practical treatment is possible even without expensive online monitoring. On the other hand by way of an improved localization one may also achieve a significantly lower thermal loading of the tissue located in front with the simultaneous necrotization of the tumor, and thus the pause time between the individual necrosis spots may be significantly reduced. This finally should lead to an optimization of the USTT which is rendered noticeable in the practical handling of the therapy and well as contributing to the further care of the patient.

The object is achieved by a method for producing a local temperature increase within a body of material using focused sound signals in a target region. wherein the target region comprises a volume situated proximate to the focus of the focused sound signals, said method including the steps of generating a sound signal in the target region by radiating the sound signal from a sound emitter in response to a pressure-time signal such that a pressure-time course of the sound signals in the target region is not sinusoidal and such that a magnitude of the pressure amplitude of the sound signal in the target region is larger than the expansion amplitude of the sound signal in the target region, wherein the pressure-time signal is not a single sinusoidal pressure-time signal, and adapting the pressure-time signal such that the pressure-time course of the sound signals in the target region is adapted to a specific utilization of the non-linear propagation and attenuation properties of the material in the target region such that an increase in the temperature in the target region produced by the adapted pressure-time signal is greater than a temperature increase produced by a sinusoidal pressure-time signal having the same power.

DETAILED DESCRIPTION

According to the invention, thus for the increased production of heat as a result of acoustic absorption such sound signals are generated in the target area which are radiated by an individual sound emitter and which are not produced by way of the radiation of a single sinusoidal pressure-time signal, and whose pressure-time course in the target region is neither sinusoidal nor has the same magnitude of pressure and expansion amplitudes, but are designed in a manner such that the magnitudes of the pressure amplitude are larger than those of the expansion amplitudes and that the pressure-time course with respect to the idle pressure condition of the material is designed adapted asymmetrically to the non-linear elastic and non-linear absorbing properties of the material to the extent that, with the focused propagation of sound in cooperation with the non-linear elastic and non-elastic absorbing properties of the material, it produces a local gain in heating in the target region in comparison to sinusoidal signals having the same power.

The pressure-time course in the target region may alternatively be created by way of the superposition of several mono-frequency signals, by way of producing asymmetrical sound signals and by way of frequency-modulated chirp signals which in each case are delivered by a sound emitter.

On the other hand the pressure-time course in the target region may be created by superposition of asymmetrical sound signals with at least one mono-frequency sound signal or by way of superposition of frequency-modulated chirp signals with at least one mono-frequency signal.

The focusing of the sound signals may be carried out by way of a self-focusing arrangement, a reflector-focusing arrangement or also with a lens-focusing arrangement.

A piezoelectric emitter is suitable for the production of the pressure-time course in the target region, which is equipped with piezoceramics with natural resonances which differ from one another, for producing at least two different sound signals acting simultaneously in the target region. A piezoelectric emitter is also suitable which comprises at least two zones for producing at least two different sound signals acting in the target region.

The method according to the invention which may also be combined with a picture-providing method, may be applied to biological materials such as by way of extra-corporal treatment of living beings, in particular within the framework of a minimal invasive treatment for the local temperature increase of body tissue. The method according to the invention however may also be applied to technical (industrial) materials in which in the region of a target region one is to produce locally limited increases of temperature.

It is generally known that the non-linear steepening effects of the US waves which the application of highly intensive ultrasound entails, has the result of an energy transfer of acoustic energy from the base frequency of the wave to higher harmonic frequency components. FIG. 3 shows this non-linear steepening process which leads to a deformation of the wave profile. An initial sine signal is deformed with an increasing advance, wherein an amplitude steepening occurs at the forward wavefront. Furthermore, these high-frequency components of the sound field on account of the damping which increases exponentially with an increasing frequency are more heavily damped by soft tissue [2]. In combination, the non-linear propagation of sound and the tissue damping thus leads to a non-linear increase of the induced heat wherever non-linearly steepened sound waves are present [9, 6, 4].

By way of the application of focusing US emitters one basically achieves an increase in the pressure amplitude which generally leads to non-linear US effects chiefly in the focus and pre-focus region. Simultaneously, the ultrasound-wave in the body tissue experiences a damping which leads to a reduction in the pressure amplitude. As long as the focusing gain exceeds the US damping in the tissue located in front one may reckon with non-linear effects in the focus region and thus with a non-linear gain in heating.

In order with mono-frequency CW signals to be able to increase the non-linear heating gain in the target region in a directed manner, deviating from the "optimal" settings due to linear considerations, on the one hand the base frequency of the signal must be reduced in order to minimize the US damping in the tissue located in front. Simultaneously however, on the other hand the pressure amplitude at the emitter must be increased in order in the focus region to produce a sufficient pressure amplitude for non-linear steepening effects. Basically thus the localization of the heating may be increased in a practically infinite manner. From a practical point of view however, that which limits this is the exceeding of the mechanical loading threshold by the expansion components of the sound wave. This leads to undesired cavitation effects which lead to mechanical destruction of tissue in the tissue located in front. With the application of mono-frequency CW signals as has been usual until now, the exploitation of non-linear effects has thus hardly been possible in practice.

A practical realization of optimizing the localization of heating is represented in the patent application WO 93/19705. Here, a non-linear heating gain is achieved by way of the confocal superposition of two ultrasound beams of spatially separated US emitters which leads to non-linear intermodulation products in the focus.

The core of the method according to the invention lies in not only accepting this heating caused by non-linear effects as being unavoidable, but using it as a non-linear heating gain in a targeted and controlled manner for optimizing the USTT in order to improve the localization of the heating and thus the complete USTT, and achieving this in that for the targeted forcing of the non-linear propagation and absorption effects in the focus region, one applies alternative emitter signals (in contrasts to mono-frequency CW signals) which, although having non-linear amplitude effects, do not lead to a mechanical overloading by cavitation. In contrast to the manner of proceeding which is described in the application WO 93/19705, here the non-linear heating gain is not achieved by way of the superposition of several separate US beams, but rather the alternative emitter signals are designed specially such that with a direct radiation from a single US emitter they lead to a non-linear heating gain in the focus.

The essential advantages of this invention lie in the fact that the non-linear heating gain is not achieved by way of the radiation of mono-frequency CW signals, but by way of the application of alternative signal forms (shapes) for heating. These are conceived such that on the one hand the loading (thermal, mechanical) of the tissue located in front is reduced, on the other hand simultaneously however that significantly more US energy is converted by way of a non-linear heating gain in the target region. This leads to an improvement of the localization which simplifies the practical metering of the therapy in particular with deeper lying tumors, or permits the gentle treatment without requiring an expensive online monitoring concept for the [closed-loop] control. FIG. 4 by way of example shows that an increase of the localization by way of the application of alternative signal forms (shapes) is possible (the results are those of a simulation tool which has been specially developed for this). In contrast to WO 93/19705, by way of the application of a single emitter, the practical handling of the therapy apparatus is simplified. A confocal alignment of the individual emitters as is required with the subject matter of the application WO 93/19705 is done away with. Furthermore, a system consisting of several individual emitters requires a significantly larger US entry window into the body. This is not always present, particularly for the treatment of deeply lying tissue where the targeted exploitation of the non-linear heating gain is decisive for the therapy.

Multi-frequency CW signals, pulse signals and the combination of multi-frequency signal and pulse signals are considered as alternative signal forms (shapes).

Multi-frequency CW signals (consisting of the additive superposition of at least two mono-frequency CW signals or chirp signals) display a cavitation effect which is changed with regard to mono-frequency CW signals [10] [3] [5]. Depending on the selection of the frequencies and their combination, by way of this the pressure amplitudes may be increased without producing mechanical overload by way of cavitation. This may be exploited for a non-linear heating gain in the target region. By way of adding higher harmonic frequency components (FIG. 4, signal S 2) in comparison to the mono-frequency signal (FIG. 4, signal S 1) with the base frequency, on the one hand the expansion component of the pressure wave in the tissue may be further reduced and on the other hand simultaneously the non-linear steepening process may be forced, and specifically on reduction of the radiated US power. By way of a superposition of the base frequency and a lower frequency component (FIG. 4, signal S 3) in the tissue located in front on account of the weak US absorption of the low-frequency component, hardly any additional heating is produced, and by way of the additional pressure field in the target region which is produced by the concentration of the lower frequency component, the main field with the base frequency is brought into the non-linear region, which leads to a significant improvement of the localization. The amplitudes of the two frequency components are selected such that each signal per se would cause no cavitation. Since all these processes are non-linear, then the additional non-linear heating produced in the focus region may be a multiple of the linearly produced heating and thus dominate the behavior of the therapy.

With the transition of CW signals to pulse signals, one then furthermore obtains the advantage that the superposition by way of interferences occurring with the CW signal, which in the regions of constructive interference lead to an increased thermal and mechanical loading in the tissue located in front, may be avoided. By way of this with the pulse signal for the same expansion loading as with the CW signal, the pressure amplitude at the emitter may be doubled which leads to a drastically increased non-linear steepening of the wave in the target region. Furthermore the pulse signal in contrast to the CW signal offers a lot of free space for forming the pulse. By way of pulse forming (shaping) in the pulse signal, one may separate the positive component which is responsible for the non-linear wave steepening, from the expansion component which represents the cause for the mechanical loading of the tissue located in front. Thus a targeted amplification of the non-linear propagation may be effected by way of a short, strong excess pressure pulse followed by a long, drawn-out but only weak vacuum pressure component. This is not possible with the application of CW sine signals. A heating is effected by way of a high-rate pulse repetition frequency of larger than 1 kHz. The use of conventional pressure pulses from the field of lithotripsy are not suitable as alternative signal forms. These pulse forms are not conceived for heating and already with pulse repetition frequencies of a few Hz lead to an increased cavitation on account of their large expansion components. Pulse repetition rates of larger than 1 kHz which are necessary for heating may thus not be employed.

Finally by way of the combination of mono-frequency or multi-frequency CW signals and pulses one may achieve an optimization. Heating is effected by way of the pulses. The (low-frequency) CW pressure field by way of its focusing in the focus and pre-focus region produces a pressure bias so that the non-linearities in the US propagation are further amplified by way of this.

LITERATURE

[1] D. R. Daum and K. Hynynen. A 256-element ultrasonic phased array system for the treatment of large volumes of deep seated tissue. *IEEE Trans. Utlras. Ferro. Freq. Control*, 46(5):1254-1268, 1999.

[2] F. A. Duck. *Physical Properties of Tissue*. Academic Press, London, 1990.

[3] R. Feng, C. Zhu, J. Xu, Z. Chen, and H. Li. Enhancement of ultrasonic cavitation yield by a bifrequency irradiation and its frequency effect. In P. K. Kuhl and L. A. Crum, editors, *Proceedings of the 135th Meeting of the ASA*, Seattle, USA, volume III, pages 1715-1716. Acoustical Society of America, Juni 1998.

[4] E. A. Filonenko. Effect of acoustic nonlinearity on heating of biological tissue by high-intensity focused ultrasound. *Acoustical Physics*, 47(4):468-475, 2001.

[5] K. Fujimoto, Y. Ishibashi, M. Shibata, T. Suzuki, S. Aida, N. Ioritani, S. Shirai, and S. Orikasa. A new cavitation suppression technique for local ablation using high-intensity focused ultrasound. *In IEEE Ultrasonics Symposium—1995*, pages 1629-1632, 1995.

[6] S. Ginter. Numerical simulation of ultrasound-thermotherapy combining non-linear wave propagation with broadband soft-tissue absorption. *Ultrasonics*, 37:693-696, 2000.

[7] C. R. Hill. Optimum acoustic frequency for focused ultrasound surgery. *Ultrasound Med. and Biol.*, 20(3):271-277, 1994.

[8] C. R. Hill and G. R. ter Haar. Review article: High intensity focused ultrasound—potential for cancer treatment. *Brit. J. Radiol.*, 68(816):1296-1303, 1995.

[9] V. Khokhlova, O. Sapozhnikov, Yu. Pishchalnikov, T. Sinilo, E. Filonenko, M. Bailey, and L. Crum. Enhancement of ultrasound-induced heating in tissue phantoms due to formation of shocks: experimental measurements and numerical simulations. Handout: WFUMB 2000, Florence, 2000.

[10] B.-Y. Lu, W.-L. Lin, Y.-Y. Chen, R.-S. Yang, T.-S. Kou, and C.-Y. Wang. A multifrequency driving system for ultrasound hyperthermia. *IEEE Engineering in Medicine and Biology*, 18(5):106-111, 1999.

[11] G. O. N. Oosterhof, E. B. Cornel, G. A. H. J. Smits, F. M. J. Debruyne, and J. A. Schalken. Influence of high-intensity focused ultrasound on the development of metastases. *European Urology*, 32(1):91-95, 1997.

[12] R. Rastert, I. Simiantonakis, M. Moosmann, P. Huber, J. Debus, and, J. Jenne. Treatment acceleration by modification of sound fields and sonication modatities. In S. C. Schneider, M. Levy, and B. R. McAvoy, editors, *IEEE Ultrasonics Symposium,* San Juan, Puerto Rico, volume 2, pages 1441-1444. IEEE Ultrasonics, Ferroetectrics and Frequency Control Society, October 2000.

[13] I. H. Rivens, R. L. Clarke, and G. R. ter Haar. Design of focused ultrasound surgery transducers. *IEEE Trans. Ultras. Ferro. Freq. Control*, 43(6):1023-1031, 1996.

[14] G. Vallancien, E. Chartier-Kastler, N. Bataille, D. Chopin, M. Hargouni, and J. Bougaran. Focused extracorporeal pyrotherapy. *European Urology*, 23 (suppl. 1), 1993.

[15] F. Wu, W.-Z. Chen, J. Bai, J.-Z. Zou, Z.-L. Wang, H. Zhu, and Z.-B. Wang. Pathological changes in human malignant carcinoma treated with High-Intensity Focused Ultrasound. *Utrasound Med. and Biol.*, 27(8):1099-1106, 2001.

What is claimed is:

1. A non-invasive method for producing a local temperature increase within a body of material using focused sound signals in a target region, wherein the target region comprises a volume situated proximate to the focus of the focused sound signals, said method comprising:
   generating a sound signal in the target region non-invasively by radiating a sound signal from a sound emitter, which is not a single sinusoidal pressure-time signal, such that a pressure-time course of said sound signal in the target region is non-sinusoidal and such that a magnitude of a pressure amplitude of said sound signal in the target region is larger than an expansion amplitude of said sound signal in the target region; and
   adapting the pressure-time signal by utilization of non-linear propagation and attenuation properties of the body of material such that the non-invasively produced local temperature increase in the target region of the body of material produced by the adapted pressure-time signal is greater than a temperature increase produced by an emitted single sinusoidal pressure-time signal having the acoustical same power.

2. The method of claim 1, wherein the pressure-time course of the sound signal radiated from the sound emitter includes several superimposed mono-frequency signals.

3. The method of claim 1, wherein the pressure-time course of the sound signal radiated from the sound emitter includes asymmetrical sound signals.

4. The method of claim 1, wherein the pressure-time course of the sound signal radiated from the sound emitter includes frequency-modulated chirp signals.

5. The method of claim 1, wherein the pressure-time course of the sound signal radiated from the sound emitter includes asymmetrical sound signals superimposed with at least one mono-frequency signal.

6. The method of claim 1, wherein the time-pressure course of the sound signal radiated from the sound emitter includes frequency-modulated chirp signals superimposed with at least one mono-frequency signal.

7. The method of claim 1, wherein the step of generating is effected on biological materials containing the target region.

8. The method of claim 1, wherein the step of generating is effected on one of technical and industrial materials containing the target region.

9. The method of claim 1, wherein said step of generating comprises effecting an extra-corporal treatment on living beings containing the target region.

10. The method of claim 1, wherein said step of generating includes effecting a minimal evasive treatment on living beings containing the target region.

11. The method of claim 1, wherein said step of generating comprises focusing the sound signal using a self focusing arrangement.

12. The method of claim 1, wherein said step of generating comprises focusing the sound signal using a reflector-focusing arrangement.

13. The method of claim 1, wherein said step of generating comprises focusing the sound signal using a lens-focusing arrangement.

14. The method of claim 1, wherein said step of generating comprises producing a pressure-time course in the target region using a piezoelectric emitter equipped with piezoceramics with natural resonances which differ from one another, for producing at least two different sound signals acting simultaneously in the target region.

15. The method of claim 1, wherein said step of generating comprises producing the pressure-time course in the target region using a piezoelectric emitter having at least two zones for producing at least two different sound signals acting simultaneously in the target region.

16. The method of claim 1, further comprising the step of providing an ultrasound image using a picture-providing method.

17. The method of claim 1, wherein the sound emitter is entirely outside the body of material during the step of generating and adapting.

* * * * *